US009700407B2

(12) United States Patent
Safabash

(10) Patent No.: US 9,700,407 B2
(45) Date of Patent: Jul. 11, 2017

(54) AUTOMATED PRELOADED INTRAOCULAR LENS INJECTOR

(71) Applicant: Abbott Medical Optics Inc., Santa Ana, CA (US)

(72) Inventor: Jason Safabash, Mission Viejo, CA (US)

(73) Assignee: ABBOTT MEDICAL OPTICS INC., Santa Ana, CA (US)

( * ) Notice: Subject to any disclaimer, the term of this patent is extended or adjusted under 35 U.S.C. 154(b) by 253 days.

(21) Appl. No.: 14/196,096

(22) Filed: Mar. 4, 2014

(65) Prior Publication Data

US 2014/0257317 A1 Sep. 11, 2014

Related U.S. Application Data

(60) Provisional application No. 61/772,858, filed on Mar. 5, 2013.

(51) Int. Cl.
*A61F 2/16* (2006.01)

(52) U.S. Cl.
CPC ............ *A61F 2/1678* (2013.01); *A61F 2/167* (2013.01); *A61F 2/1662* (2013.01); *A61F 2/1672* (2013.01)

(58) Field of Classification Search
CPC .... A61F 2/1662; A61F 2/1672; A61F 2/1678; A61F 2/167; A61F 2/1664; A61F 2/1667; A61F 2/1675; A61F 2/1691; A61F 2002/1681; A61F 2002/1682; A61F 2002/1683; A61F 2002/1686; A61F 2002/1689; A61F 2002/169; A61F 2002/16901; A61F 2002/16902; A61F 2002/16903; A61F 2002/16905;
(Continued)

(56) References Cited

U.S. PATENT DOCUMENTS

| 2,472,116 | A | * | 6/1949 | Maynes | A61M 5/20 604/136 |
| 4,681,102 | A | * | 7/1987 | Bartell | A61F 2/1678 606/1 |
| 5,474,562 | A | | 12/1995 | Orchowski et al. | |
| 5,702,402 | A | | 12/1997 | Brady | |
| 6,045,567 | A | * | 4/2000 | Taylor | A61B 5/150022 600/573 |
| 6,293,925 | B1 | * | 9/2001 | Safabash | A61M 5/158 604/136 |
| 2004/0147938 | A1 | | 7/2004 | Dusek et al. | |
| 2005/0154399 | A1 | | 7/2005 | Weber et al. | |

(Continued)

FOREIGN PATENT DOCUMENTS

EP 1857074 A1 11/2007
EP 1941846 A1 7/2008
(Continued)

OTHER PUBLICATIONS

International Search Report and Written Opinion for Application No. PCT/US2014/020138, mailed on May 26, 2014, 11 pages.

*Primary Examiner* — Jonathan Miles
*Assistant Examiner* — Kankindi Rwego
(74) *Attorney, Agent, or Firm* — Abbott Medical Optics Inc.

(57) ABSTRACT

This intraocular lens (IOL) injector for delivering an IOL into an eye of a patient includes an IOL load chamber and connected delivery tube, and a spring-loaded push rod for urging the IOL through the delivery tube and out of a distal tip thereof. The injector includes an actuator that is cocked to compress an automatic delivery coil spring. Cocking the actuator also folds the IOL and may elongate a dual optic IOL. A braking mechanism may be provided to permit control of the spring-biased IOL advancement. The injector is in a pen style with finger plates on the side for better ergonomic control.

6 Claims, 15 Drawing Sheets

(58) Field of Classification Search
CPC ........ A61F 2002/169051; A61F 2002/169052;
A61F 2002/169053; A61M 5/20; A61M
5/31501; A61M 5/31595; A61M
2005/202; A61M 2005/2086; A61M
2005/3115; A61M 2005/3143; A61B
5/150106; A61B 5/150137; A61B
5/150167; A61B 5/15019; A61B
5/150198; A61B 5/150206; A61B
5/150259; A61B 5/15103; A61B 5/15105;
A61B 5/15107; A61B 5/15192; A61B
5/15198
USPC ........................................................ 623/6.12
See application file for complete search history.

(56) References Cited

U.S. PATENT DOCUMENTS

2010/0217273 A1\* 8/2010 Someya ................ A61F 2/1678
606/107
2011/0264101 A1\* 10/2011 Inoue .................... A61F 2/1678
606/107

FOREIGN PATENT DOCUMENTS

EP             2340786 A1    7/2011
WO    WO-2011155636 A1   12/2011

\* cited by examiner

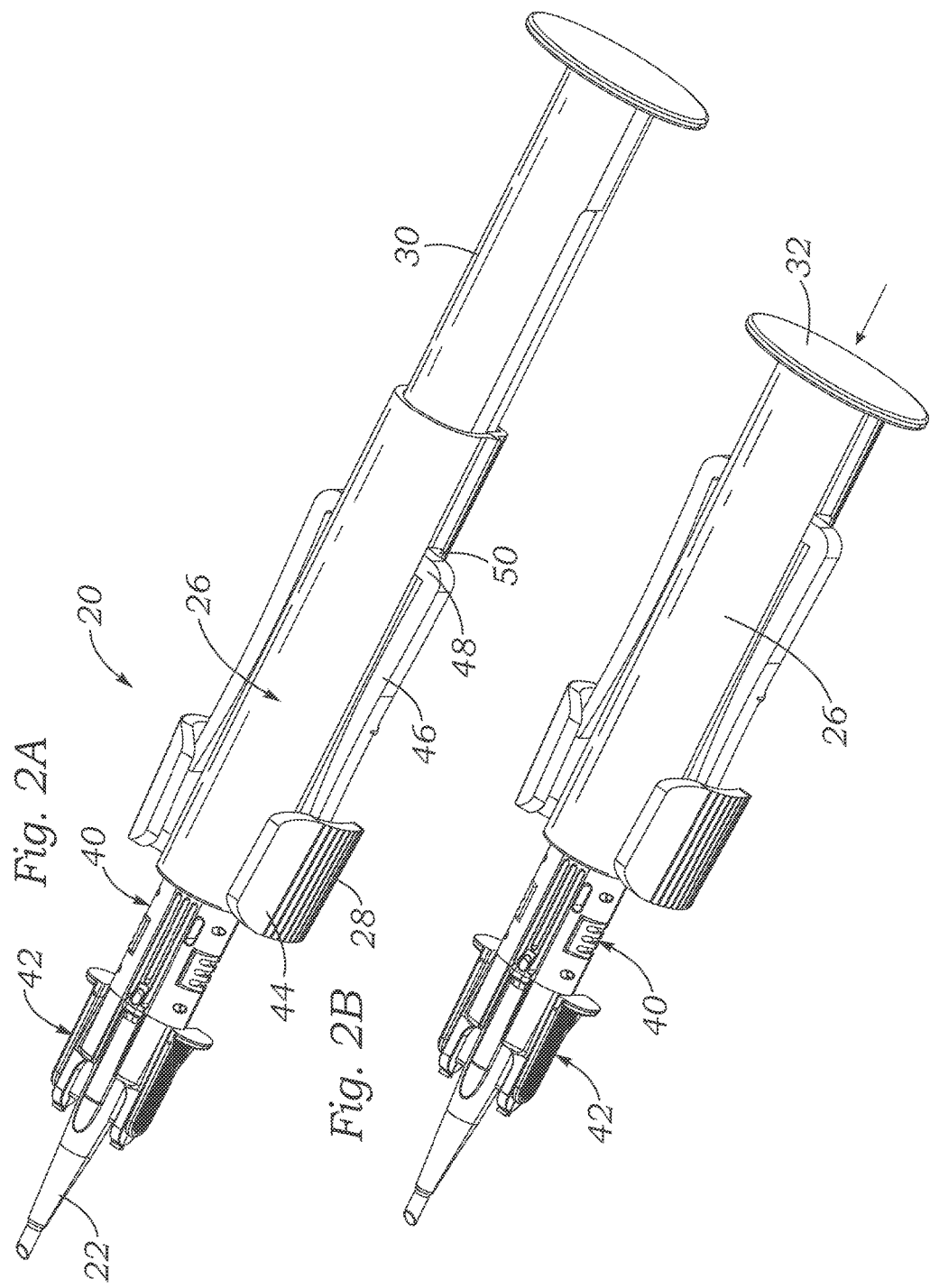

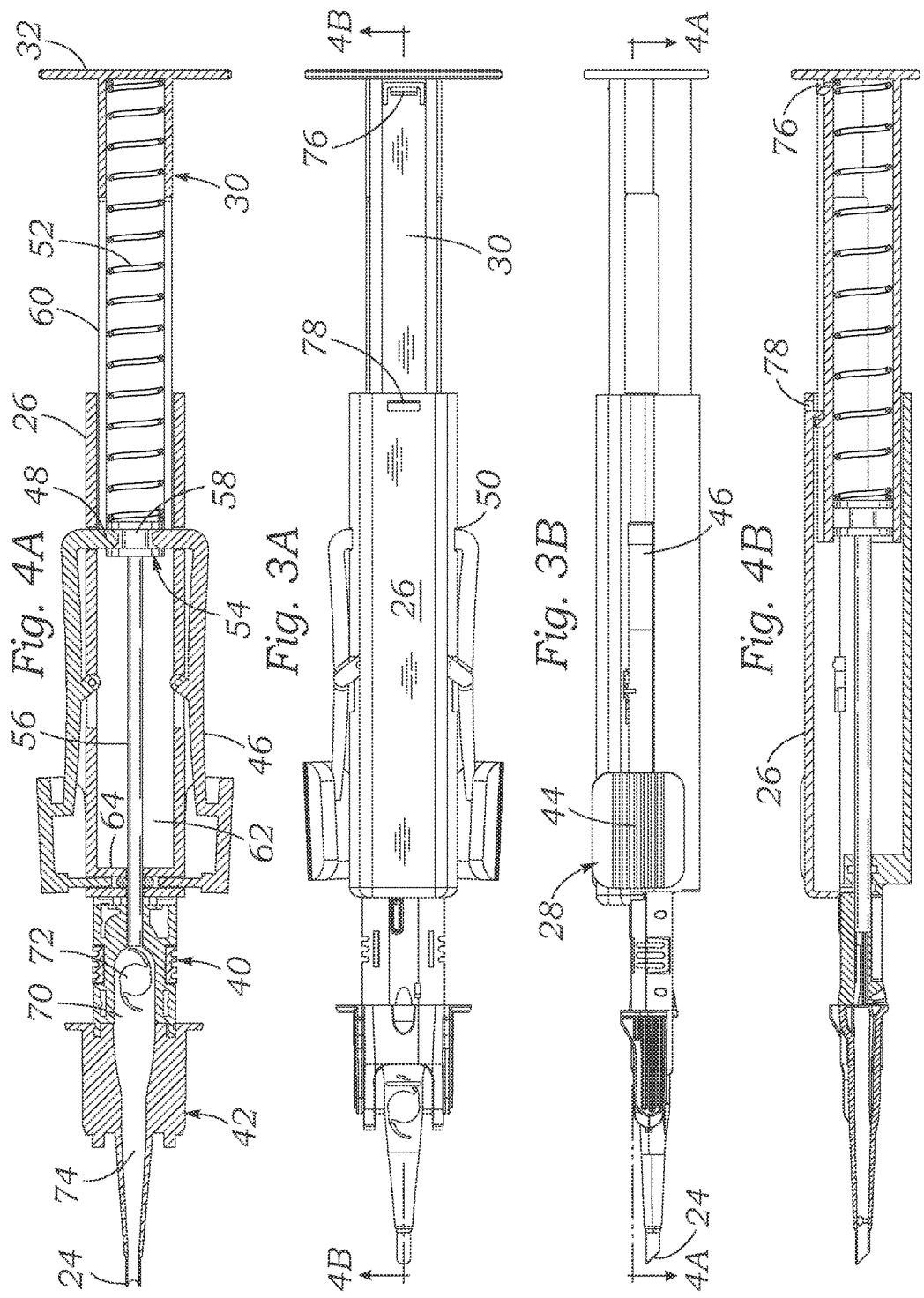

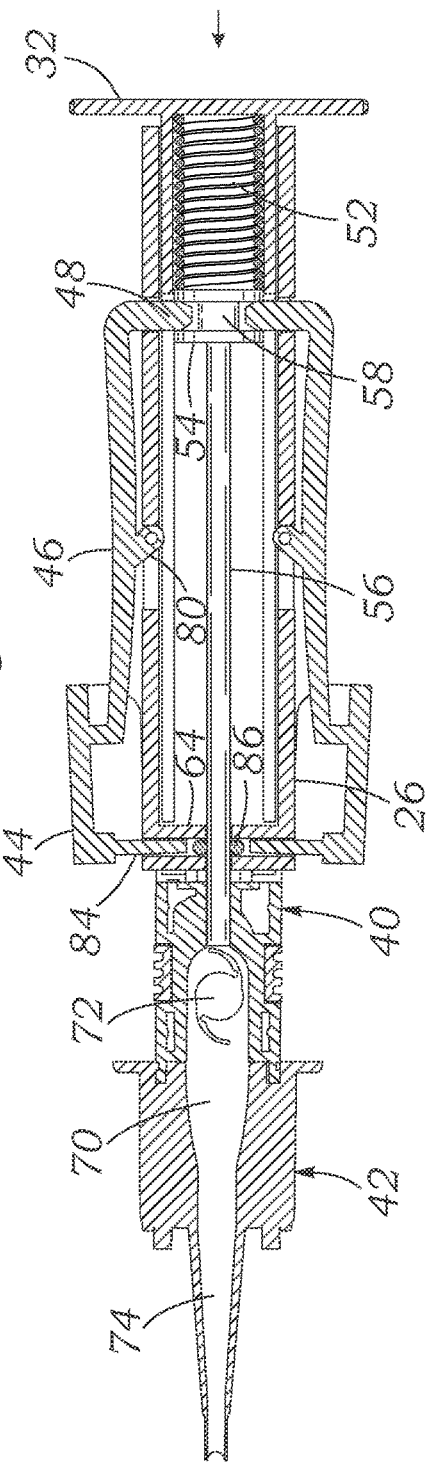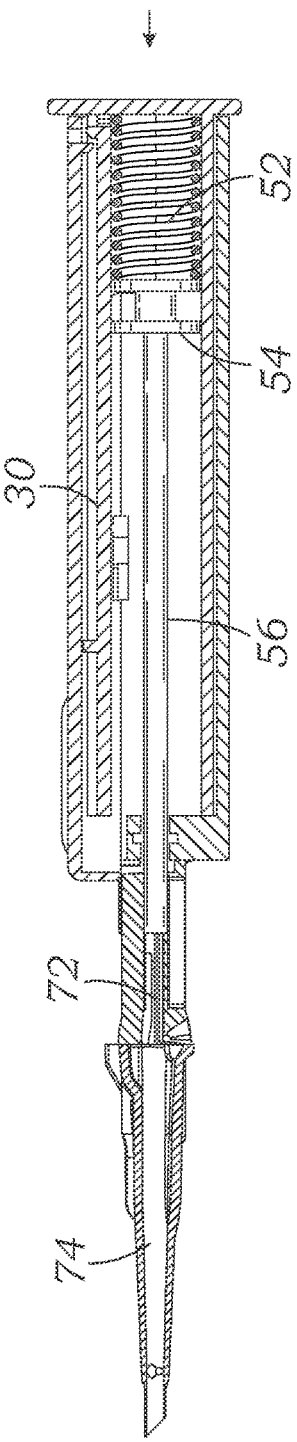

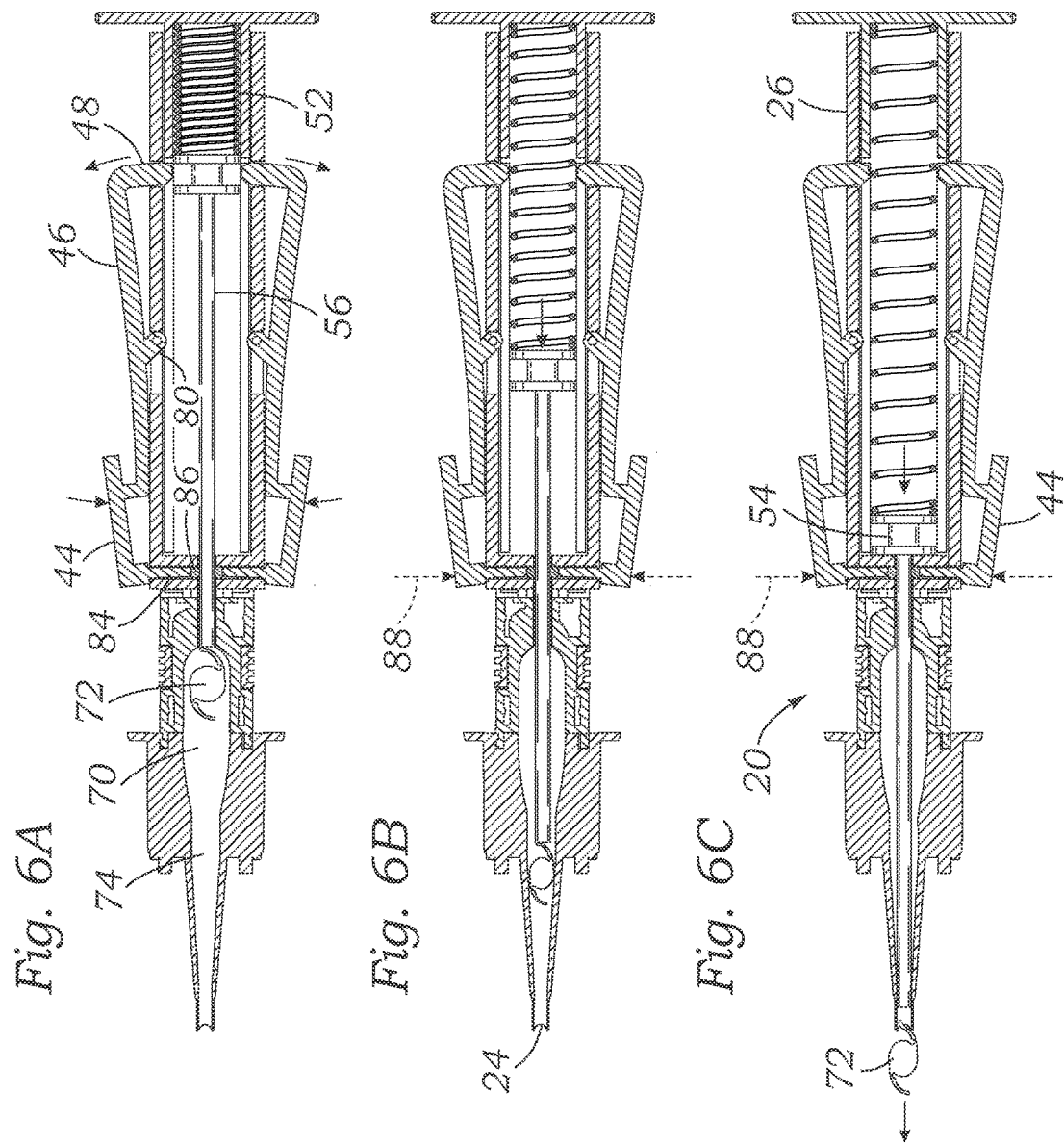

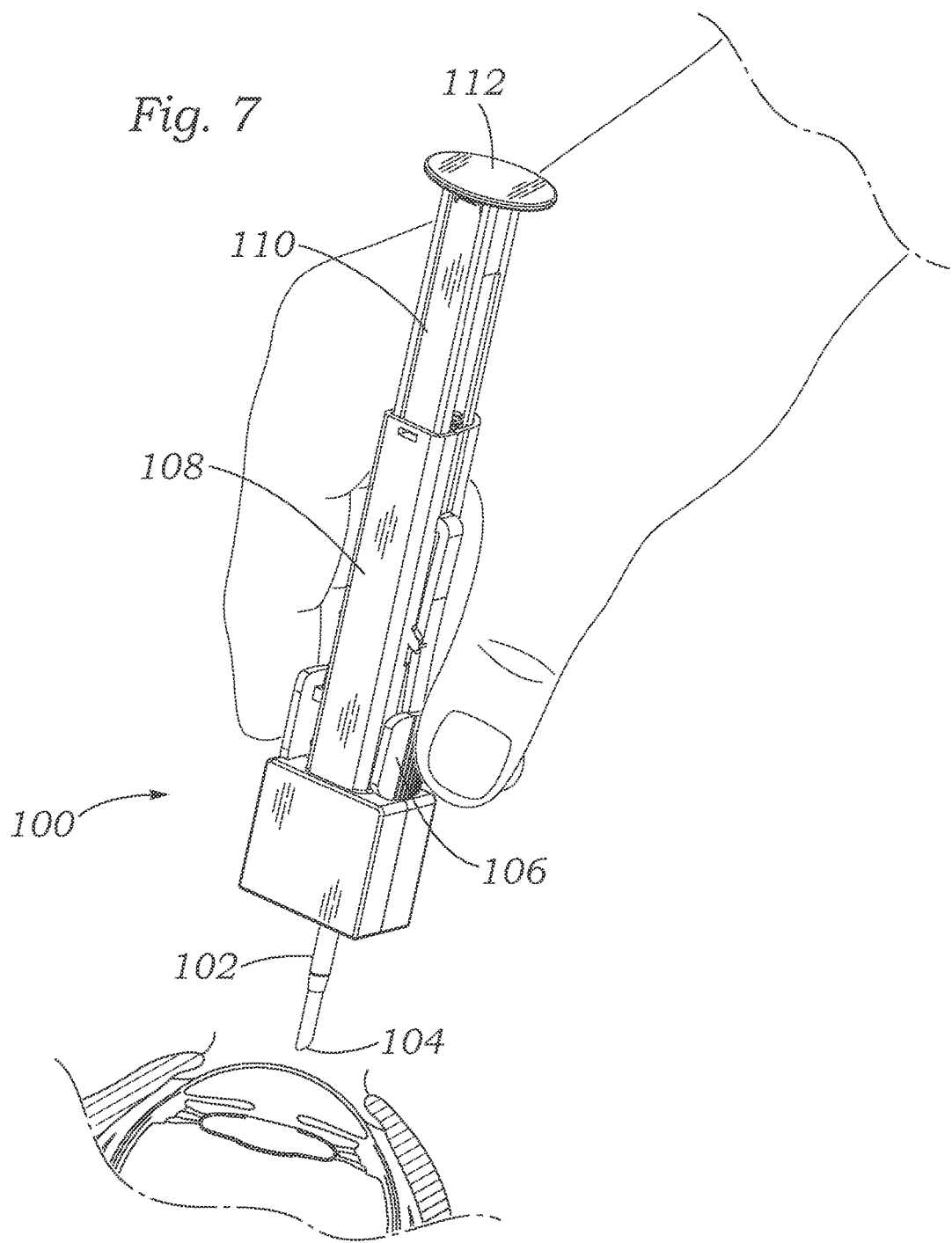

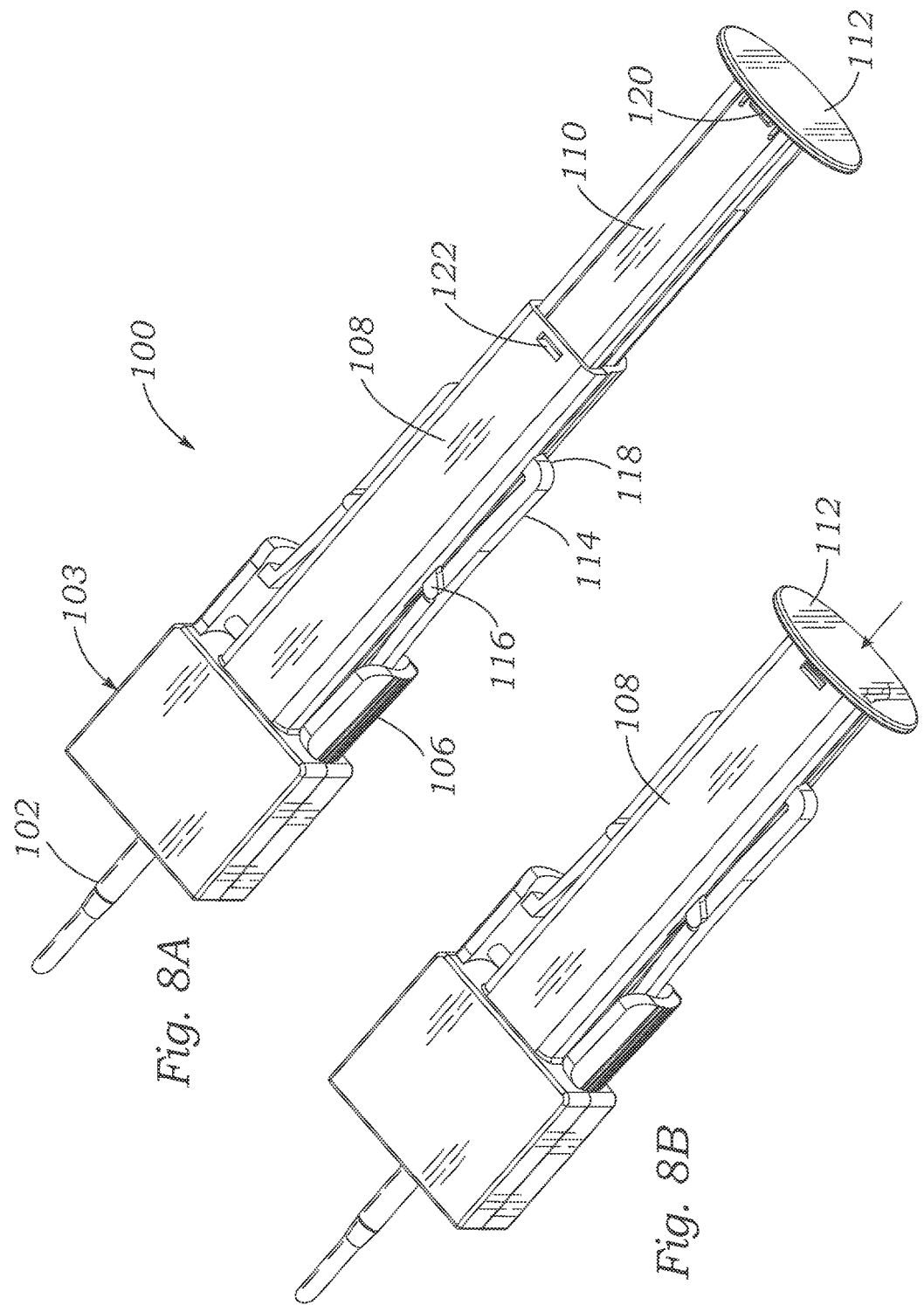

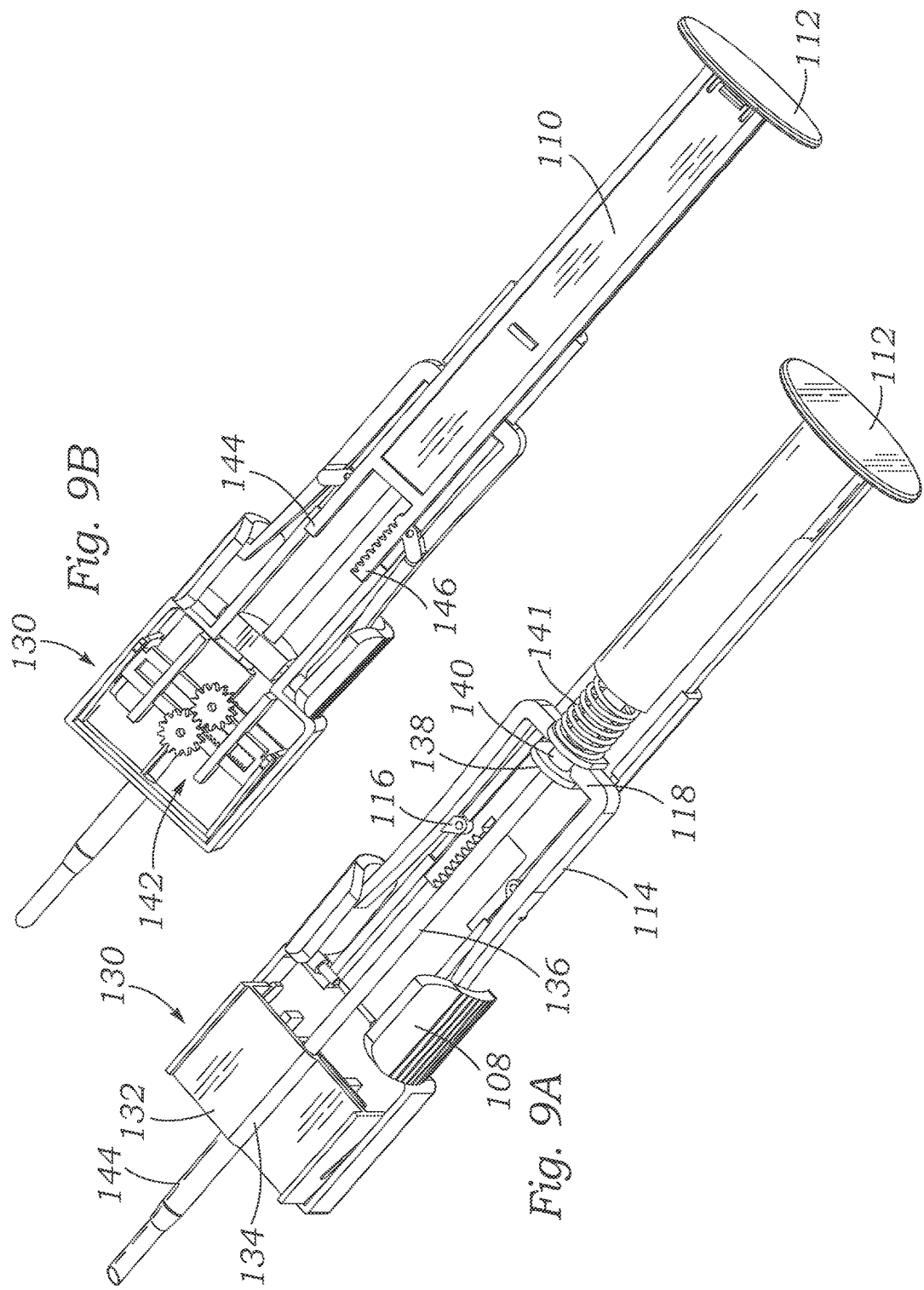

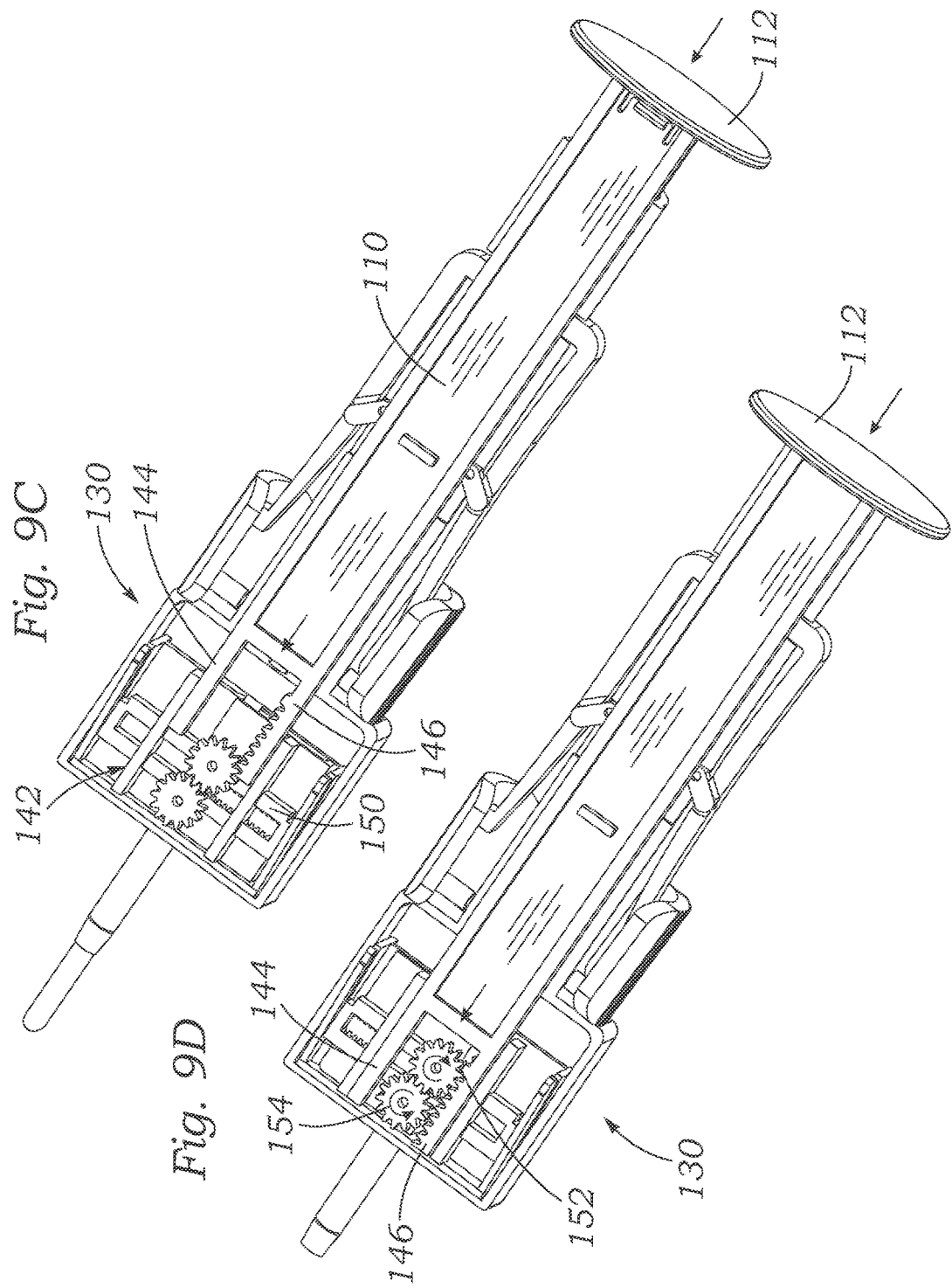

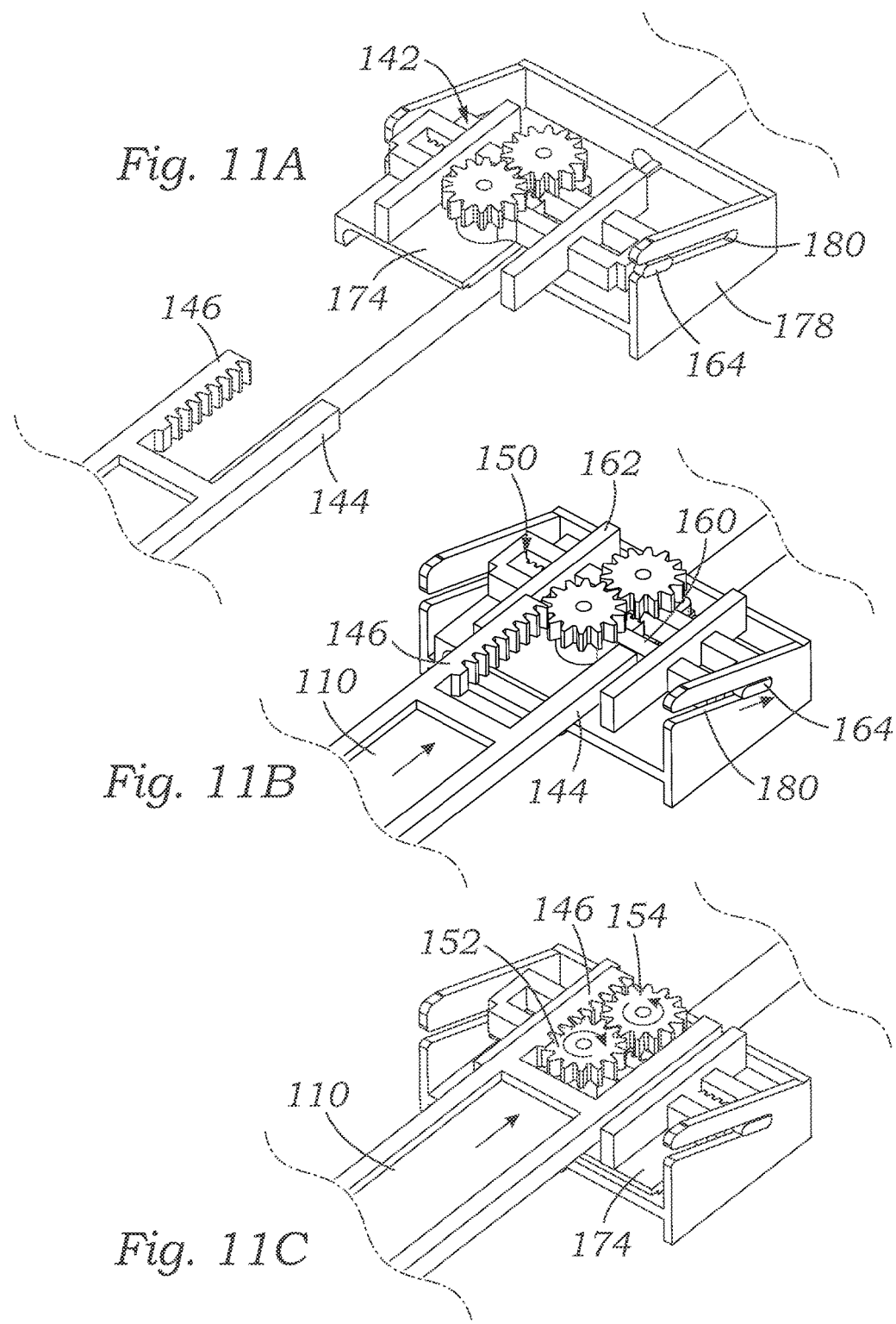

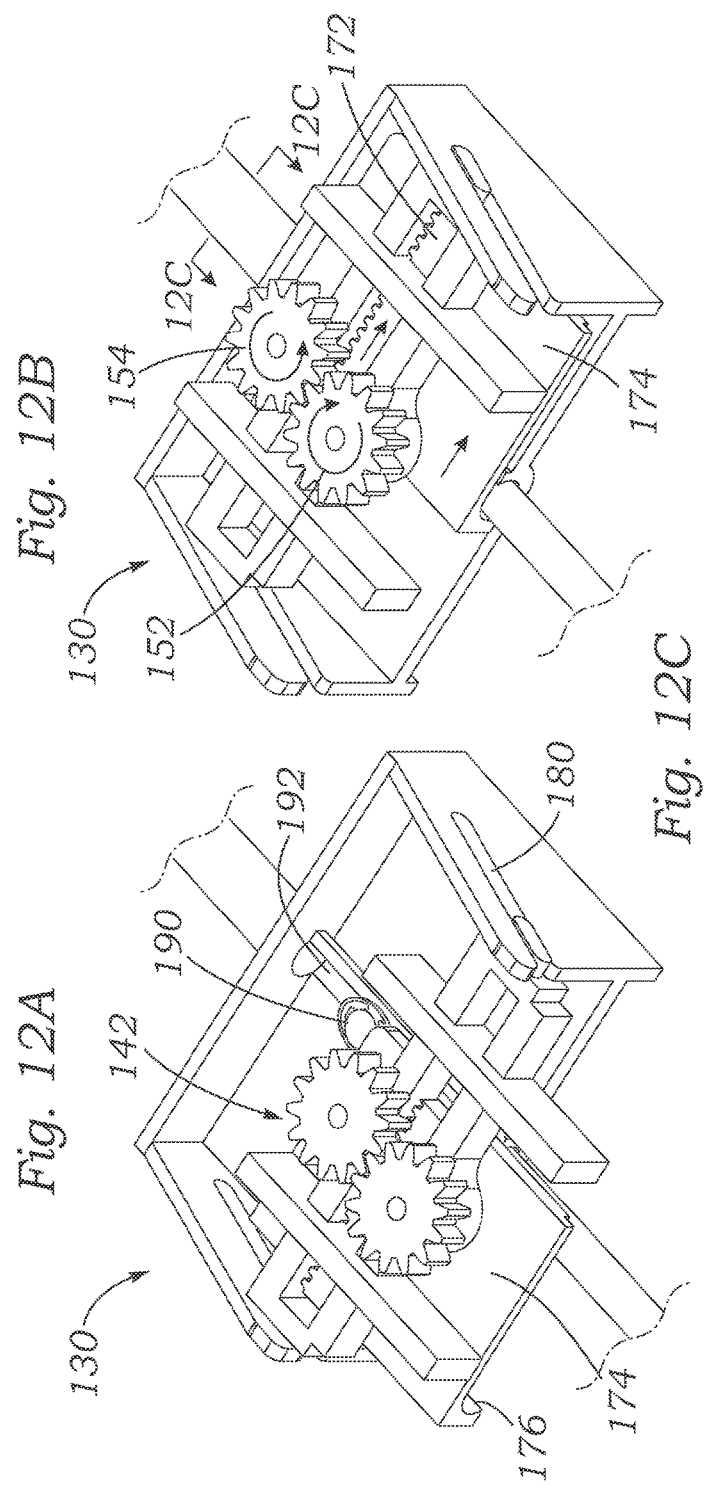

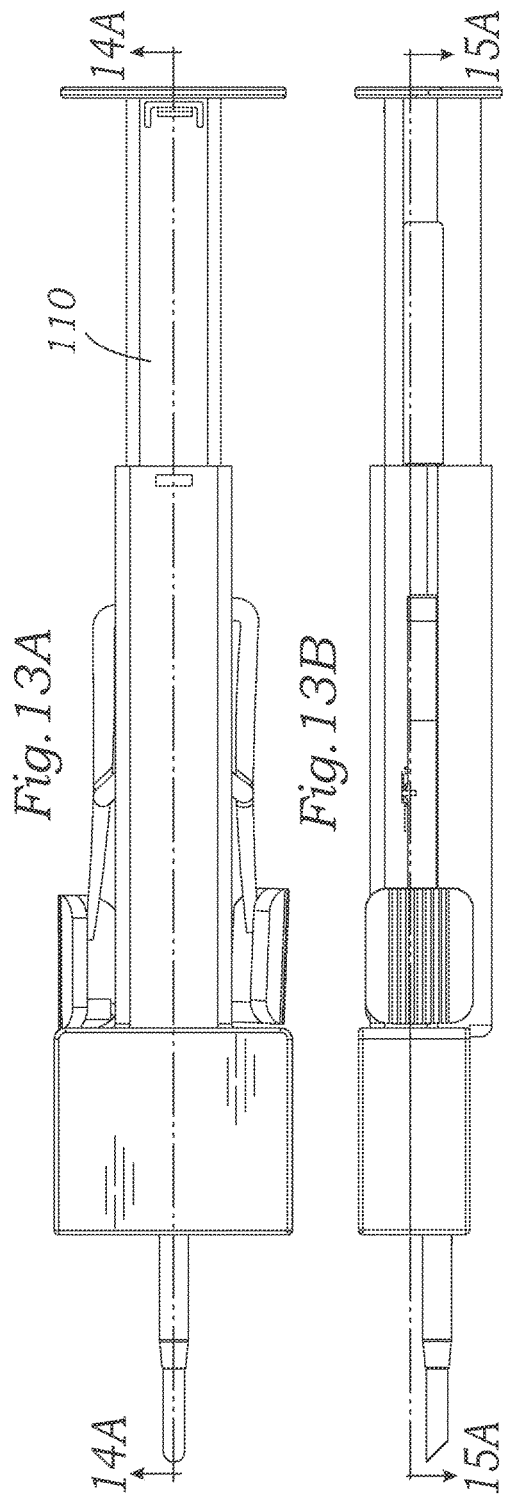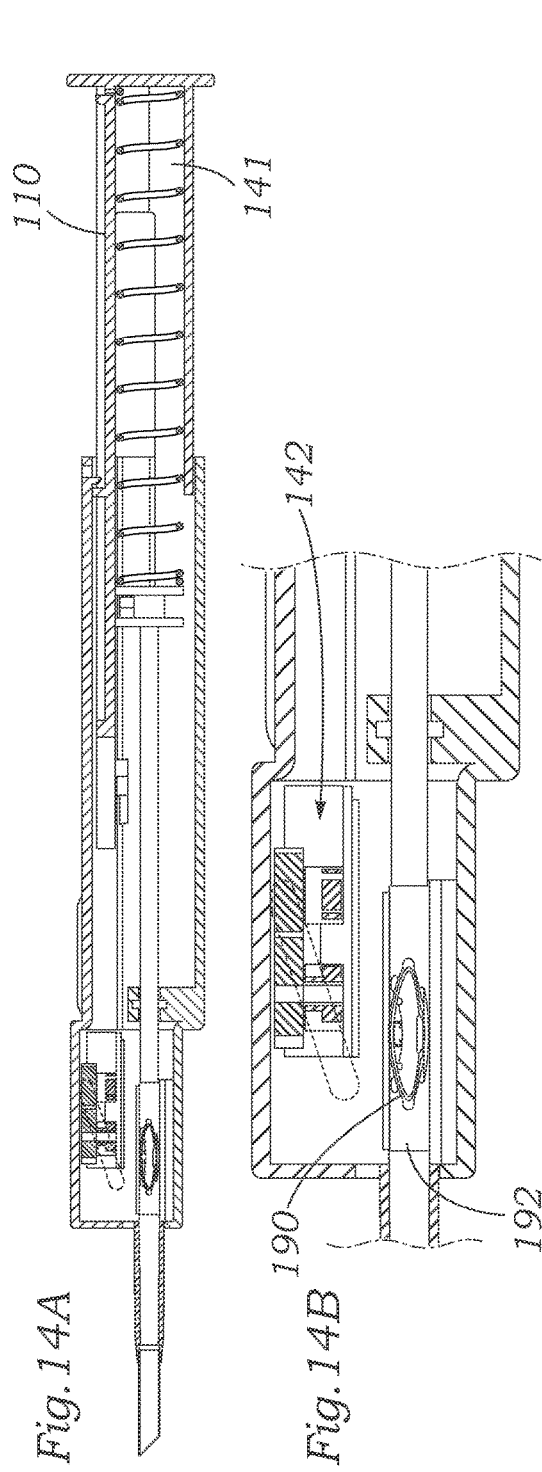

AUTOMATED PRELOADED INTRAOCULAR LENS INJECTOR

CROSS-REFERENCES TO RELATED APPLICATIONS

This application claims priority to U.S. provisional application No. 61/772,858 filed on Mar. 5, 2013, the entire contents of which are incorporated herein by reference.

FIELD OF THE INVENTION

The present invention relates to systems and methods for delivering an intraocular lens (IOL) into an eye through an injector and, more particularly, to devices and methods for automating ejection of an IOL from an injector.

BACKGROUND OF THE INVENTION

It is estimated that at least about 42% of Americans between the ages of 52 and 64 and 73% of Americans between the ages of 65 and 74 get cataracts. A cataract is a clouding of the eye's lens that impairs a person's vision and, if left untreated, causes blindness. As a result, each year approximately 1.4 million people in the United States alone undergo cataract surgery, whereby the clouded lens is removed and replaced with an intraocular lens (IOL) implant.

A typical IOL includes an optic or lens body for focusing light toward the retina of the eye abd one or more fixation members or haptics extending outward from the optic for securing and centering the IOL in the desired position within the chamber of the eye. The IOL is implanted directly into the eye through a small incision in a way that reduces trauma and expedites post-surgery healing. To fit through this small incision, modern IOLs are designed to be deformed, e.g., rolled, folded or the like, to a relatively small profile and then allowed to return to their original shape within the eye.

A useful technique for inserting an IOL into the eye includes use of an IOL injector. Injectors for delivering IOLs into the eye typically employ a handpiece and a cartridge having a hollow, tapered insertion tube or cannula through which the folded IOL is passed using a push rod. The distal end of the cartridge insertion tube is beveled into a sharp point that enables insertion through the corneal incision and facilitates expulsion and manipulation of the IOL into the capsular bag. The cartridges are made of disposable materials, such as plastics, and remain in a sterile package until ready for coupling with the handpiece. Some injectors do without the cartridge, and may be reusable.

Conventional IOL cartridges include a load chamber connected to an injection tube. In many popular versions, such as in U.S. Pat. No. 4,681,102 to Bartell or U.S. Pat. No. 5,702,402 to Brady, the load chamber is formed by two hinged halves which receive the IOL, and which close to fold the IOL. A non-folding cartridge is seen in U.S. Pat. No. 5,474,562 to Orchowski in which forceps are used to insert the IOL into a proximal or rear opening of the cartridge. After mating the cartridge with the handpiece (if a separate cartridge is used), a push rod urges the IOL through the cartridge insertion tube into the eye. Typically, the load chamber is first partially filled with a liquid or gel, for example, a viscoelastic medium such as a sodium hyaluronate gel. The viscoelastic facilitates passage of the IOL through the injector, and in some cases the tip of the push rod does not directly contact the IOL, but instead engages the intermediate viscoelastic so as to distribute hydraulic pressure across the IOL and cause it to proceed through the injector and into the eye.

Some recent IOL injectors or cartridges are preloaded with an IOL to eliminate the steps associated with mating the IOL with the cartridge. Despite the reduction in complexity, preloaded injectors often require numerous steps to complete delivery, making it a difficult training challenge. Moreover, the syringe-style injector may be somewhat awkward to hold and the plunger advancement may be hard to control, leading to forceful ejections of the IOL, for example.

There remains a need for devices and methods that simplify the process of loading an IOL cartridge and provide improved control to the delivery system.

SUMMARY OF THE INVENTION

In accordance with one aspect, the present application discloses a preloaded single-use pen-type IOL injector for single optic lenses with an automatic drive mechanism that includes a spring-loaded actuator to drive the plunger and injector lens. Ergonomically placed release buttons enable single handed insertion and eliminate the need to push on the end of the plunger. These release buttons automatically release the plunger and move the lens forward. The release mechanism is supplemented with a braking mechanism to control the speed of delivery with the same buttons. The IOL injector thus provides precise control using automated delivery and improved ergonomics in a pen-shaped device that can be held easily by one hand.

In accordance with another aspect, the present application discloses a preloaded single-use injector for dual-optic lenses. The injector enables one-handed insertion and involves just three steps to complete the IOL delivery. An injector actuator is displaced to simultaneously fold the dual optic lens and cock the device by loading a spring mechanism which will drive the IOL plunger forward automatically. Ergonomically located release buttons release the plunger to start delivery, and may be coupled with a braking mechanism to provide positive feedback and controlled delivery. Again, the dual-optic lens injector provides precise control with an automated delivery and improved ergonomics that enable one-handed operation.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts:

FIGS. 2A and 2B are perspective views of the IOL injector of FIG. 1 showing an actuator retracted and depressed, respectively;

FIGS. 3A and 3B are top plan and side elevational views of the IOL injector of FIG. 1 with the actuator refracted;

FIGS. 4A and 4B are longitudinal sectional views through the IOL injector of FIG. 1, taken along lines 4A and 4B of FIGS. 3B and 3A, respectively;

FIGS. 5A and 5B are longitudinal sectional views similar to FIGS. 4A and 4B but showing the actuator depressed to preload an internal spring used for automatic advancement of an IOL push rod;

FIGS. 6A-6C are longitudinal sectional views similar to that of FIG. 5A and showing operation of the automatic advancement of the push rod to eject an IOL out of a distal delivery tip;

FIG. 7 is a perspective view of another exemplary IOL injector according to one embodiment of the invention being used to insert an intraocular lens (IOL) into a patient's eye;

FIGS. 8A and 8B are perspective views of the injector of FIG. 7 showing an actuator retracted and cocked, respectively;

FIG. 9A is a perspective view of a bottom side of the injector of FIG. 7 with an outer housing cover removed to show internal details;

FIGS. 9B-9D are perspective views of the top side of the injector of FIG. 7 with an outer housing cover removed to show internal details of an IOL folding mechanism during a sequence where the actuator moves from its retracted to its cocked position, illustrating engagement of actuator rails with a slide rail and eventually a pinion gear on the slide rail;

FIGS. 11A-11C are perspective views showing distal advancement of the actuator rails and movement of the slide rail down a housing ramp and lateral movement of a lower slide plate caused thereby;

FIGS. 12A and 12B are enlargements of the IOL folding mechanism in the same positions as in FIGS. 11A and 11C, while FIG. 12C is an end view of a delivery tube showing rolling of a dual optic IOL therein;

FIGS. 13A and 13B are top plan and elevational views of the injector of FIG. 7 with the actuator in the retracted position;

FIG. 14A is a vertical longitudinal sectional view through the injector taken along line 14A-14A of FIG. 13A, while FIG. 14B is an enlarged view of an IOL load chamber and associated IOL folding mechanism;

FIG. 15A is a horizontal longitudinal sectional views through the injector of FIG. 7 taken along line 15A-15A, while

FIG. 16A is a vertical longitudinal sectional view through the injector of FIG. 7 taken along line 16A-16A of FIG. 15B, while

DETAILED DESCRIPTION OF THE PREFERRED EMBODIMENTS

The present invention facilitates the process of delivering an intraocular lens (IOL) into a patient's eye using an injector. The IOL is typically implanted using an injector that rolls, folds, or otherwise configures the lens for delivery through a small incision in the eye in a way that reduces trauma and expedites post-surgery healing. The IOL is positioned in a cartridge having a load chamber mounted in the injector and injected into the eye through a delivery tube having a beveled tip. The injector, cartridge and/or delivery tube are first partially filled with a liquid or gel lubricating agent, for example a viscoelastic material.

Figure 1:
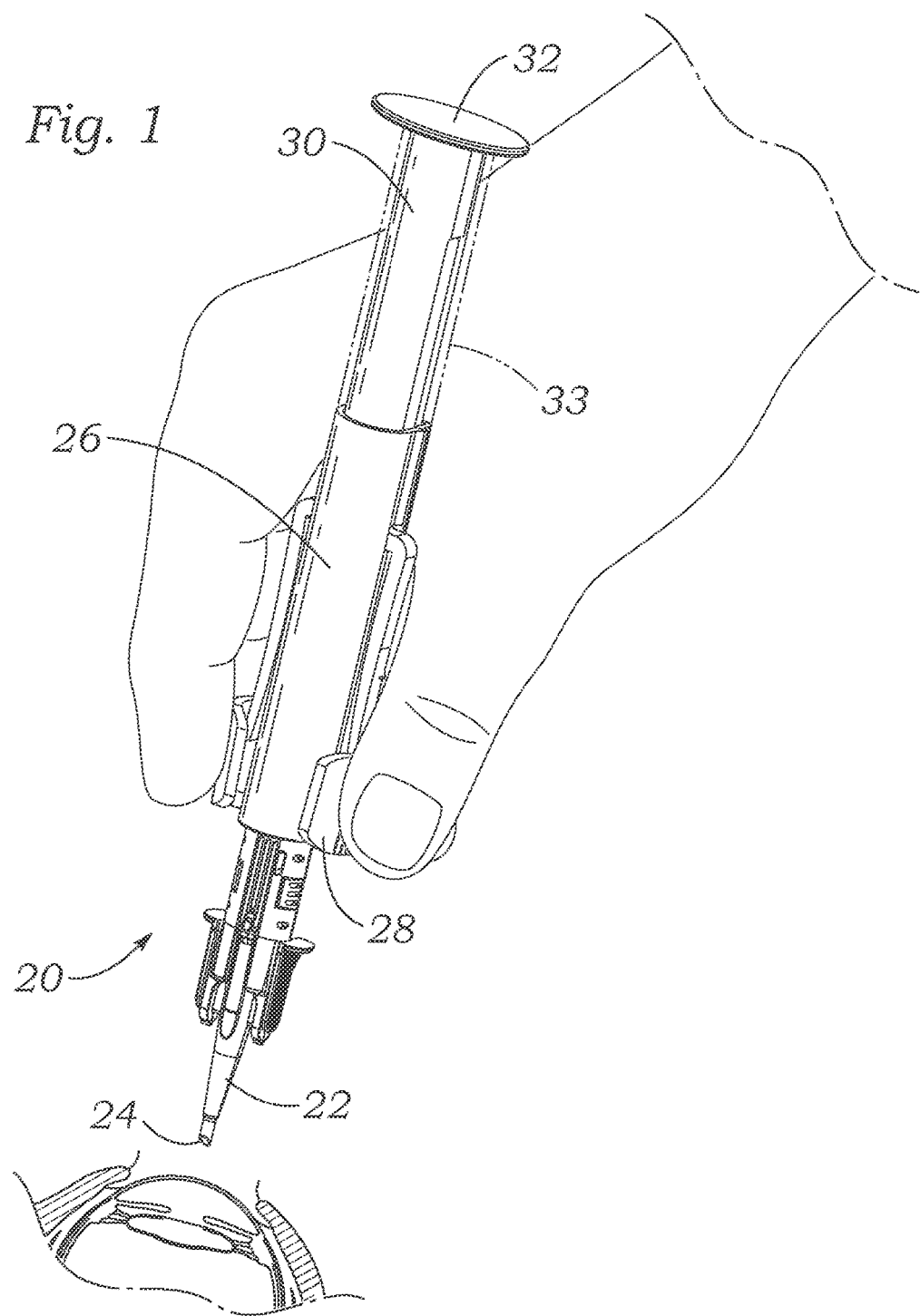
FIG. 1 is a perspective view of an exemplary injector according to one embodiment of the invention being used to insert an intraocular lens (IOL) into a patient's eye.

As seen in FIG. 1, an exemplary pen-style IOL injector 20 is shown as would be held by a surgeon during implantation of an intraocular lens (IOL) into a patient's eye such as during cataract surgery. The various steps in preparing the eye for such surgery will not be described in great detail herein, but typically involve forming one or more incisions in the eye to allow the introduction of surgical instruments. The surgeon then removes the anterior face of the capsule that contains the lens inside the eye, and removes the natural lens material using a phacoemulsification technique in anticipation of implanting the replacement IOL.

The IOL injector 20 has a pen-style configuration with a distal delivery tube 22 terminating in a beveled distal tip 24, a central housing 26 having a pair of opposed triggers 28 for operating the injector, and an actuator 30 extending from a proximal end of the housing and terminating in a thumb plate 32. The surgeon can hold the injector 20 like a pen by the opposed triggers 30 in an ergonomically optimal way for manipulating the delivery tube 22 into the eye. As will be described below, the triggers 30 are used to both initiate an automated injection of the IOL through the delivery tube 22 as well as control its velocity.

With reference also to FIGS. 2A and 2B, the housing 26 of the IOL injector 20 has a generally cylindrical outer shape and attaches on its distal end to a load station 40 which, in turn, attaches to a distal cartridge 42 from which the delivery tube 22 projects. As will be shown, the IOL resides within a load chamber inside a load station 40 which is aligned with the delivery tube 22 of the cartridge 42. The housing 26, load station 40, and cartridge 42 are fixed together and packaged as an assembly.

FIGS. 2A and 2B show the opposed triggers 28 formed by convex grooved finger plates 44 located near a proximal end of the central housing 26, each attached to an elongated lever arm 46. The proximal end of each of the lever arms 46 terminates in an inwardly directed finger 48 that passes in through a side aperture 50 in the housing 26. A mid-portion of each of the lever arms 46 connects to the housing 26 at a fulcrum, such that squeezing the finger plates 44 causes outward movement of the fingers 48 from the apertures 50. As will be explained, the fingers 48 provide latches that prevent movement of an internal IOL push rod until the finger plates 44 are squeezed.

The actuator 30 is shown in FIG. 2A in a retracted position, and in a cocked position in FIG. 2B, displaced distally such that all but the thumb plate 32 is received within the housing 26. FIG. 1 shows a removable safety sheath 33 that may be assembled at the time of manufacture to prevent inadvertent depression of the actuator 30. At the time of use, and when the surgeon requires the actuator 30 to be pressed into its cocked position, the safety sheath 33 is removed and discarded.

Now with reference to FIGS. 3A/3B and 4A/4B, certain internal structural details will be described. First, the actuator 30 comprises a generally hollow body that closely receives a coil spring 52 therein. One end of the coil spring 52 abuts the inside of the thumb plate 32, while the other end contacts a plunger head 54 on the proximal end of a push rod 56. The plunger head 54 has a spool-like configuration with proximal and distal flanges defining a recess 58 therebetween sized to receive both of the inwardly directed fingers 48. When the fingers 48 reside in the recess 58 they prevent axial movement of the push rod 56.

A pair of elongated slots 60 seen in FIG. 4A extend along the majority of the length of the actuator 30 aligned with the inwardly directed fingers 48 on opposite sides of the actuator. The slots 60 permit the actuator 30 to be pushed into a chamber 62 defined within the housing 26 against the compressive force of the coil spring 52.

FIGS. 4A and 4B show the push rod 56 extending distally through a bore in a distal wall 64 of the housing 26, and a short distance into the load station 40, terminating just short of a load chamber 70. An IOL 72 resides within the load chamber 70. In the illustrated embodiment, the IOL 72 has a single lens with a pair of arcuate haptics to the front and back. The injector 20 disclosed in FIGS. 1-6 can be used to deliver a variety of IOLs. The load chamber 70 opens to and is aligned with a tapered delivery channel 74 extending through the cartridge 42. As will be seen, the push rod 56 has a length sufficient to urge the IOL 72 through the entire delivery channel 74 and out of the distal tip 24.

FIG. 3A shows a small locking tab 76 at a proximal end of the actuator 30, just distal to the thumb plate 32. When the actuator 30 is depressed, the locking tab 76 eventually engages a complementary locking recess 78 formed in a proximal end of the housing 26. While the fingers 48 on the lever arms 46 engage the recess 58 of the plunger head 54, the left end of the coil spring 52 is fixed while the right end is compressed by the thumb plate 32. The locking tab 76 and locking recess 70 prevent the actuator 30 from springing backwards from the force of the compressed spring 52.

As mentioned, depressing the actuator 30 moves it to its cocked position as shown in FIGS. 5A and 5B. In this state, the coil spring 52 is maximally compressed, and the actuator 30 is locked in position by engagement between the locking tab 76 and recess 78. This configuration can be enabled in advance of the actual surgery, as the position of the lever arms 46 maintains the initial position of the push rod 56. In the cocked position of the actuator 30, the coil spring 52 is preloaded for automatic advancement of the push rod 56 and ejection of the IOL 72. The distal end of the push rod 56 is shown just behind the IOL 72, poised to urge it through the delivery channel 74. Prior or subsequent to cocking the actuator 30, a quantity of viscoelastic medium is introduced into the load chamber 70 and along the delivery channel 74.

Before a discussion of the automatic ejection of the IOL 72, further details of the lever arms 46 require explanation. Namely, as best seen in FIG. 5A, each of the lever arms 46 includes an inward fulcrum projection 80 that pivots about a point fixed on the outside of the housing 26. The shape of the lever arm 46 is slightly concave to the outside, and squeezing the finger plates 44 causes the left end of the arms to move inward and the right ends with the fingers 48 to move outward. Additionally, the finger plates 44 each have a braking finger 84 projecting inwardly into a channel (not numbered) formed in the distal wall 64 of the housing 26. An O-ring 86 closely surrounds the push rod 56 within the channel such that the inward ends of the fingers 84 contact the O-ring when the finger plates 44 are squeezed.

FIGS. 6A-6C illustrate operation of the automatic advancement of the push rod 56 to eject the IOL 72 out of the distal delivery tip 24. First, as seen in FIG. 6A, the user begins by squeezing the finger plates 44 such that the lever arms 46 pivot about the fulcrum projection 80 and the proximal fingers 48 retract from their positions holding the push rod 56 in position, as depicted by the movement arrows.

Release of the push rod 56 allows the coil spring 52 to expand, thus driving the plunger head 54 and push rod 56 in a distal direction, which urges the IOL 72 from the load chamber 70 and into the delivery channel 74. This period of advancement of the IOL 72 is seen in FIG. 6B. During advancement of the push rod 56 and IOL 72, the surgeon can apply opposite inward forces on the finger plates 44 as indicated by the dashed arrows 88 to slow down the velocity of the push rod. That is, the braking fingers 84 eventually contact the outside of the O-ring 86 which, in turn, squeezes on the push rod 56 and exerts friction thereto. Indeed, the surgeon can completely halt advancement of the IOL 72 by fully squeezing inward on the finger plates 44.

Furthermore, an emergency stop mechanism (not shown) can also be included in the injector 20 to immediately halt advancement of the push rod 56 if the surgeon completely releases pressure completely on the finger plates 44. For example, a structure on the proximal end of the lever arms 46, such as the inwardly-directed fingers 48, may interact with a structure connected to the push rod 56 to stop its movement. This additional safety feature may be desirable so that the user can quickly stop the IOL advancement in case of hazard/popping/failure, or other unforeseeable event. The push rod 56 could then be locked, or just temporarily stopped such that subsequent squeezing of the finger plates 44 re-commences push rod 56 advancement.

Finally, FIG. 6C shows the IOL 72 being ejected from the delivery tube tip 24 after the push rod 56 has advanced as far as it can go by virtue of contact between the plunger head 54 and the distal wall 64 of the housing 26. Even at the final stages of ejecting the IOL 72, the surgeon can apply the inward forces 88 on the finger plates 44 to slow down release of the IOL from the tip. After IOL implantation, the injector 20 is removed from the operating site.

FIGS. 1-6 described above pertain to an automated preloaded single lens IOL injector 20. A similar mechanism is shown in FIGS. 7-17 for a dual optic IOL. A dual optic IOL includes two lenses axially spaced apart, or vaulted, and connected by haptics. When implanted, the capsular bag and muscles connected thereto contract and expand so as to change the spacing between the two lenses, and thus change the focus. Such an IOL has slightly different considerations during implantation because of its relatively larger size along the optical axis.

FIG. 7 shows the hand of the surgeon manipulating an exemplary pen-style IOL injector 100 to insert an intraocular lens (IOL) into a patient's eye. The injector 100 includes a delivery tube 102 terminating at a beveled distal tip 104 used to enter the eye and deposit the IOL. To initiate the automated delivery of the IOL, the surgeon squeezes a pair of finger plates 106, or triggers, mounted for movement within a central housing 108. Prior to that, however, an axially-oriented actuator 110 having a proximal thumb plate 112 is converted from its retracted position as shown to a cocked position within the housing 108.

FIGS. 8A and 8B show the injector 100 of FIG. 7 with the actuator 110 retracted and cocked, respectively. As will be described below, converting the actuator 110 to the cocked position preloads a delivery spring and both elongates and folds or rolls the IOL. As with the earlier embodiment, the finger plate 106 connects to a lever arm 114 that pivots about a fulcrum projection 116 mounted for rotation about the housing 108. Each lever arm 114 includes an inwardly-directed finger 118 that acts as a latch to prevent premature ejection of the IOL. A locking tab 120 on the actuator 110 engages a locking recess 122 on the housing 108 to hold the actuator in place once it is depressed or cocked. Finally, FIG. 8A shows a load station 130 positioned between the delivery tube 102 and housing 108, details of which will be described below.

Now with reference to FIG. 9A, a bottom side of the injector 100 of FIG. 7 with outer covers for the housing 108 and load station 130 removed is shown. The bottom of the load station includes a stepped floor 132 defining a bottom portion 134 of an axially-oriented load chamber. A push rod 136 extends axially from a plunger head 138 into the load chamber. The plunger head 138 has a spool-like configuration with a central recess 140 that receives the inwardly-directed fingers 118 of the lever arms 114. In this position, the fingers 118 prevent movement of the push rod 136, in particular after the actuator 110 has been depressed to compress a coil spring 141.

FIGS. 9B-9D are perspective views of the top side of the injector 100 with outer covers removed to show internal details during a sequence where the actuator 110 moves from its retracted to its cocked position. The load station 130 contains an IOL folding mechanism 142, described in more detail below. The actuator 110 includes on its distal end a pair of actuator rails 144, 146 that engage the IOL folding mechanism 142. One of the actuator rails 146 has inwardly directed teeth which act as a driving rack for a pinion gear on the folding mechanism 142.

FIG. 9B shows the actuator 110 in its retracted position with the coil spring 141 relatively uncompressed and extending between the plunger head 138 and the inside surface of the thumb plate 112. FIGS. 9C and 9D shows the actuator 110 partly and then fully depressed, respectively, into its final cocked position. The actuator rails 144, 146 initially contact a slide rail 150 on the IOL folding mechanism 142 and push the entire mechanism down a ramp, as seen in FIG. 9C. At the bottom of the ramp, the actuator rails 144, 146 are elevated over a horizontal bar of the slide rail 150 to the level of two pinion gears 152, 154, at which time the actuator rails 46 having rack teeth rotates the first of the pinion gears 152.

Figure 10A:
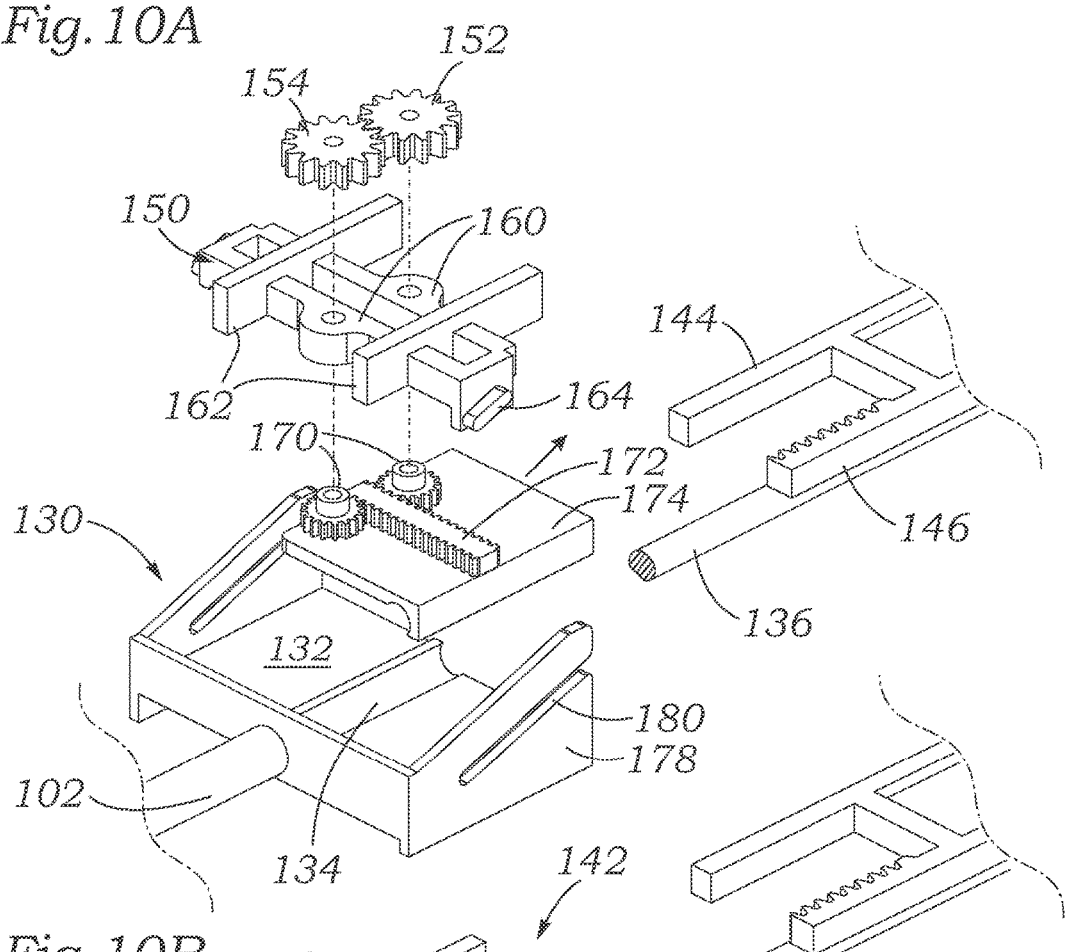
FIGS. 10A-10C are perspective exploded and assembled views of a distal portion of the injector housing having the IOL folding mechanism.
Figure 10B:
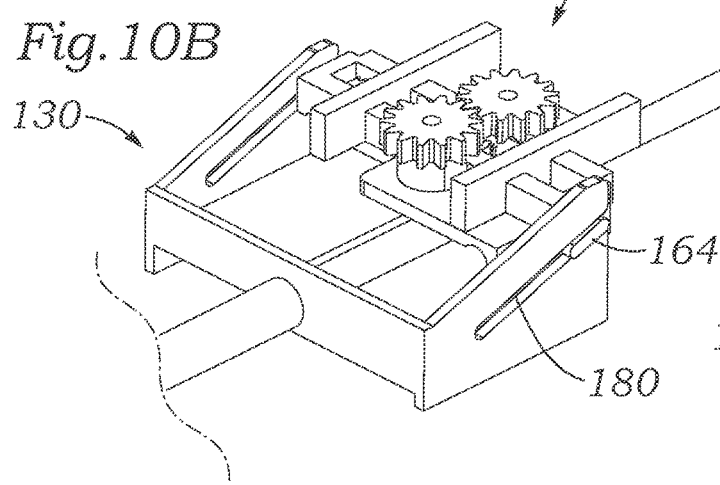
Figure 10C:
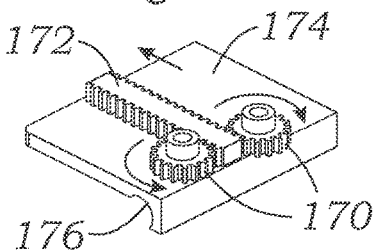

FIGS. 10A-10C are perspective exploded and assembled views of the load station 130 having the IOL folding mechanism 142 therein. The slide rail 150 includes a pair of lateral bars 160 joined at their ends and a pair of axial guides 162. Small angled ramp guides 164 project outward from both lateral sides of the slide rail 150. The two upper pinion gears 152, 154 rotate with small shafts (not shown) that extend through journal holes in the two lateral bars 160 and fix to a pair of smaller lower pinion gears 170. The lower pinion gears 170 engage oppositely-directed rows of teeth on a lateral rack 172 mounted above a slide plate 174. The slide plate 174 features a downwardly extending IOL-folding wall 176. The wall 176 has a partial circular contour that is designed to curl under the IOL and roll it upon itself. The initial position of the slide plate 174 relative to the lower pinion gears 170 is seen in FIG. 10A, corresponding to the retracted position of the actuator rails 144, 146. After the actuator rails 144, 146 have advanced to their cocked position, the lower pinion gears 170 translate the slide plate 174 laterally as seen in FIG. 10C.

The load station 130 further includes a pair of vertical walls 178 extending upward from the stepped floor 132. Each of the walls 178 has an angled guide channel 180 formed therein that receives the similarly sized and angled guides 164 on the lateral sides of the slide rail 150, as seen in FIG. 10B. The slide rail 150 remains horizontally oriented during its descent down the angled channel 180.

FIGS. 11A-11C are perspective views showing distal advancement of the actuator rails 144, 146 and movement of the slide rail 150 down the angled channel 180. The position of the IOL folding mechanism 142 at the top of the channel 180 is shown in FIG. 11A, corresponding to the retracted position of the actuator rails 144, 146. It will be noted that the slide plate 174 underneath the slide rail 150 is displaced to the left, with the IOL folding wall 176 off to the side.

FIG. 11B shows the actuator 110 axially advanced until the rails 144, 146 contact the proximal lateral bar 160. Because the bar 160 is initially at the same height as the rails 144, 146, the actuator 110 moves the folding mechanism 142 down the angled channel 180. Ultimately, the lateral bar 160 descends to a point where it is below the rails 144, 146, which is the snapshot of FIG. 11B. As will be shown below, this downward and forward movement of the slide plate 174 acts on the dual optic IOL to elongate the top lens in front of the lower lens.

Finally, FIG. 11C shows the actuator 110 fully advanced such that the rail 146 having the row of teeth engages and rotates the first upper pinion gear 152, which also rotates the second upper pinion gear 154. As described above with respect to FIGS. 10A-10C, rotation of the upper pinion gears 152, 154 also rotates the lower pinion gears 170, which in turn laterally translates the slide plate 174 into the position shown in FIGS. 10C and 11C. This causes the IOL folding wall 176 to roll the dual optic IOL into the configuration of FIG. 12C.

FIGS. 12A and 12B are enlargements of the IOL folding mechanism 142 in the same positions as in FIGS. 11A and 11C. More particularly, FIG. 12A shows the IOL folding mechanism 142 at the top of the channel 180 prior to advancement of the actuator rails 144, 146 (not shown in these views for clarity). The slide plate 174 begins at a laterally displaced position with the IOL folding wall 176 off-center. A dual optic IOL 190 is shown positioned within a load chamber 192, at the forward end of and below the slide plate 174. The same position of the IOL folding mechanism 142 at the top of the ramp and above or just back from the IOL 190 in the load chamber 192 is seen in FIG. 14A. FIGS. 13A and 13B are views of the injector 100 with the actuator 110 in the retracted position, while FIG. 14B is an enlarged view of the IOL load chamber 192 and undeformed IOL 190 therein.

The IOL injector 100 is preloaded with the IOL 190 placed in the load chamber 192. The IOL 190 may be positioned within (any of the embodiments of) the injectors disclosed herein (e.g., with the lens in the storage condition) during manufacture/assembly of the injector. The injector 100, with the IOL 190 thus disposed inside, may then be sterilized as a unit, either at the point of manufacture or at some downstream location. Where appropriate, the sterilized injector-IOL assembly may be contained in a sterile package, wrapper, bag, envelope, etc. in which the injector-IOL assembly may remain until arrival at the operating room. This facilitates a simple point-of-use procedure for medical personnel involved in implanting the IOL 190 contained in the injector 100: after opening (any) packaging, the physician, or other medical personnel, can compact and insert the IOL 190 using the injector 100 as discussed above, without (any need for) removing the IOL 190 from the injector 100. Accordingly, there is no need to handle the IOL 190 or manually load it into an insertion device at the point of use, both of which can be difficult and tedious, and can compromise the sterility of the lens.

Figure 15A:
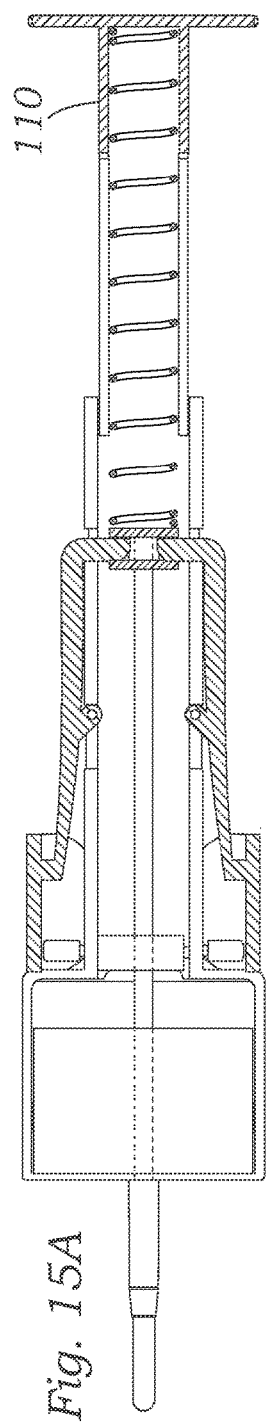
Figure 15B:
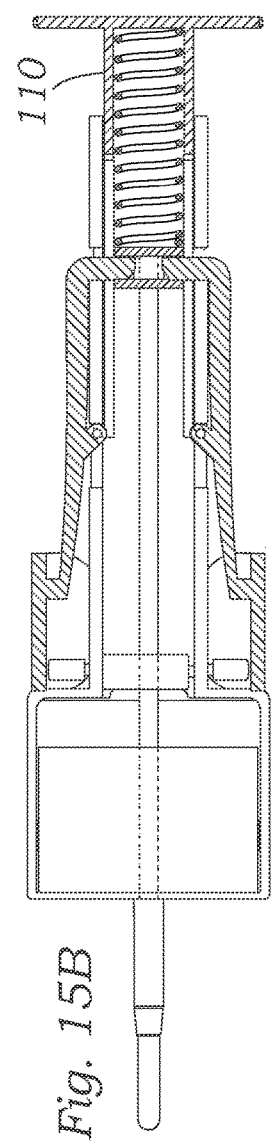
FIG. 15B is the same view with the actuator cocked.
Figure 16A:
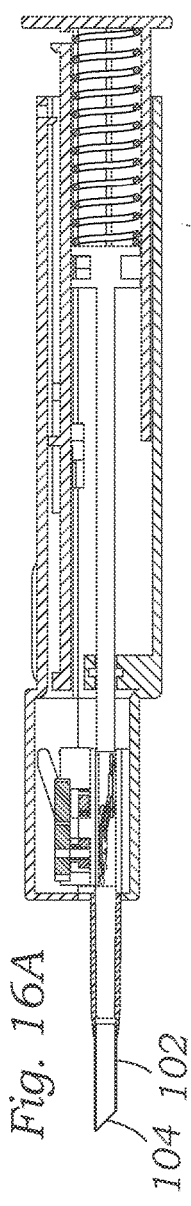
Figure 16B:
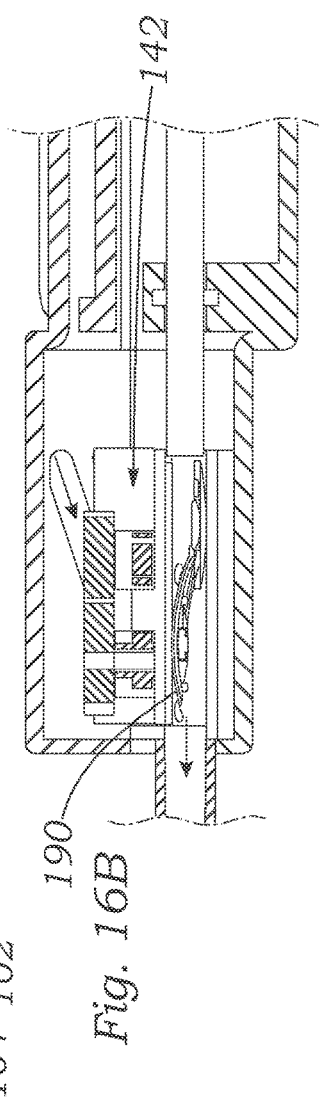
FIG. 16B is an enlarged view of an IOL load chamber and associated IOL folding mechanism.

FIG. 15A is a horizontal longitudinal sectional view through the injector 100 with the actuator 110 in its retracted position, while FIG. 15B is the same view with the actuator 110 advanced or cocked. As discussed, advancement of the rails 144, 146 moves the IOL folding mechanism 142 down the angled channel 180 from the position in FIG. 14B to the position of FIG. 16B, which causes the lower face of the slide plate 174 to contact the upper lens of the dual optic IOL 190. Forward or distal movement of the slide plate 174 displaces the upper lens relative to the lower lens, as seen in the vertical longitudinal sectional view of FIGS. 16A and 16B. In this regard, the frictional forces between the slide plate 174 and upper lens, and between the floor of the load chamber 192 and lower lens, are sufficiently large to cause this lens offset, or IOL lengthening, rather than simply pushing entire the IOL 190 in a distal direction. Ultimately, after the IOL folding mechanism 142 has descended down the ramp 180 the IOL 190 is contorted into an elongated shape with the upper lens in front of the lower lens. This elongation permits the IOL 190 to then be rolled into a smaller profile than would be possible if the dual lenses remained facing one another, which in turn permits the distal tip 104 of the delivery tube 102 to be smaller in size. As is well known, the smaller the tip 104 the smaller the incision into the eye that is created, which reduces trauma and subsequent healing time.

Again with reference to FIGS. 11C and 12B, continued advancement of the actuator 110 causes engagement between the teeth of the rail 146 with the pinion 152, which as explained causes lateral displacement of the slide plate 174. The IOL folding wall 176 moves to the center and contacts and rolls the elongated IOL 190, as seen schematically in FIG. 12C, which is looking in a proximal direction down the delivery tube 102. Cocking the actuator 110 thus prepares the IOL 190 for advancement through the delivery tube 102, and also compresses the coil spring 141 to facilitate automatic IOL advancement.

Figure 17A:
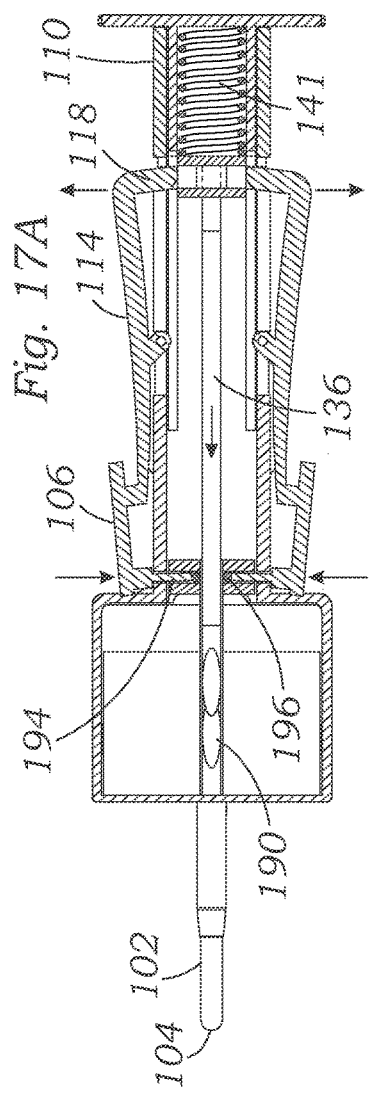
FIGS. 17A-17C are horizontal and vertical sectional views of the injector of FIG. 7 showing a sequence of positions of a push rod during automatic ejection of the dual optic IOL therein.

The cocked position of the actuator 110 is seen in FIG. 17A, with the coil spring 141 maximally compressed. As mentioned above, the inwardly-directed fingers 118 on the lever arms 114 engage the recess 140 of the plunger head 138 (such as in FIG. 15B) and act as latches to prevent premature ejection of the IOL. The fingers 118 prevent movement of the push rod 136 until the physician maneuvers the distal tip 104 into position for IOL implant. At this time, the physician squeezes the two finger plate 106 of the lever arms 114 to retract the fingers 118 from the plunger head recess 140, thus permitting the coil spring 141 to act on the distal end of the push rod 136 and displace it in a distal direction as shown. By virtue of the previously applied viscoelastic medium within the load chamber 192 and delivery tube 102, the push rod 136 does not simply propel forward and expel the IOL 190 with great velocity, but instead the process is damped by the medium and occurs relatively slowly and evenly.

Figure 17B:
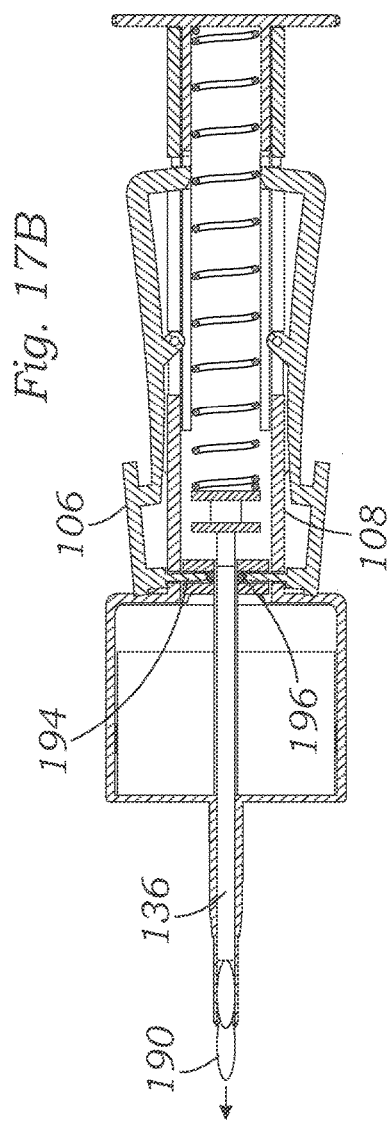
Figure 17C:
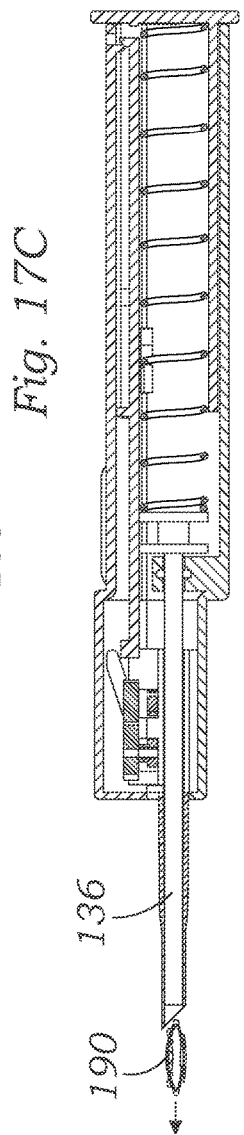

The progression of the IOL 190 down the delivery tube 102 and out of the tip 104 is shown in FIGS. 17B and 17C. If the surgeon desires to slow the IOL advancement even more, or to stop it to reposition the tip 104, for example, he/she may squeeze the finger plates 106 even further to force a braking finger 196 inwardly into a channel (not numbered) formed in the housing 108. As with the previous embodiment, an O-ring 198 closely surrounds the push rod 136 within the channel such that the inward ends of the fingers 194 contact the O-ring when the finger plates 106 are squeezed, thus frictionally slowing the push rod 136. This provides the surgeon with control of the speed of expulsion of the IOL 190 from the distal tip 104.

It is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An injector for delivering an intraocular lens (IOL) into the eye of a subject, comprising:
    a housing;
    a load chamber within the housing for holding an IOL; a delivery tube in communication with the load chamber and terminating at a distal tip;
    a push rod within the housing and movable through the load chamber for urging the IOL in a distal direction from the load chamber, through the delivery tube and out of the distal tip in a delivery procedure;
    an actuator mounted to slide within the housing;
    a biasing coil connected between the actuator and the housing, the biasing coil assuming a relaxed state when the actuator is in a retracted position and assuming a stressed configuration when the actuator is in a cocked position, the actuator and housing having cooperating features to hold the actuator in the cocked position, and the biasing coil being coupled to apply a distally-directed force to the push rod when the biasing coil is in its stressed configuration; and
    a latch that maintains the push rod in a proximal position against the force of the biasing coil, a trigger that releases the latch to permit the biasing member to apply a distally-directed force to the push rod, and an operator controlled brake associated with the trigger for slowing or halting movement of the push rod when the trigger is fully depressed;
    wherein the push rod has a proximal plunger head with a recess, and the latch comprises an inwardly-directed finger on a lever arm mounted on one side of the housing, the trigger being provided on a distal end of the lever arm and the lever arm having a fulcrum in between the trigger and inwardly-directed finger so that inward movement of the trigger causes outward movement of the latch;
    wherein there are two identical lever arms opposite each other across the housing and two associated triggers that are squeezed to each release a latch to permit the biasing coil to apply a distally-directed force to the push rod.

2. The injector of claim 1, wherein the injector has a pen-style of operation with the trigger being mounted on at least one side of the housing such that the user holds the injector and operates the trigger in the manner of holding a pen.

3. The injector of claim 1, wherein the housing further includes an IOL folding mechanism that is configured to first elongate and then fold an IOL when the actuator moves from the retracted position to the cocked position.

4. A pen-style injector for delivering an intraocular lens (IOL) into the eye of a subject, comprising:
    a housing having an IOL delivery tube on a distal end and an actuator with a thumb plate on a proximal end, the actuator being mounted to slide within the housing from a retracted position extending from the housing and a cocked position within the housing, the housing further including a spring positioned to be compressed by the actuator when moving from the retracted position to the cocked position, and the actuator and housing having cooperating features to hold the actuator in the cocked position;
    a push rod within the housing and movable through a load chamber defined therein for urging an IOL in a distal direction from the load chamber in a delivery procedure, wherein the compressed spring engages and applies a distally-directed force to a proximal end of the push rod when in its stressed configuration;
    a latch that maintains the push rod in a proximal position against the force of the spring, a trigger on the side of the housing that releases the latch to permit the spring to apply distally-directed force to the push rod, and an operator controlled brake associated with the trigger that slows the velocity of the push rod when engaged;

wherein the brake braking mechanism comprises a braking finger associated with the trigger that is configured to press against an O-ring surrounding the push rod and apply friction thereto.

5. The injector of claim 4, wherein the push rod has a proximal plunger head with a recess, and the latch comprises an inwardly-directed finger on a lever arm mounted on one side of the housing, the trigger being provided on a distal end of the lever arm and the lever arm having a fulcrum in between the trigger and inwardly-directed finger so that inward movement of the trigger causes outward movement of the latch.

6. The injector of claim 4, wherein the housing further includes an IOL folding mechanism that is configured to first elongate and then fold an IOL when the actuator moves from the retracted position to the cocked position.

\* \* \* \* \*